(12) United States Patent
Tanaka et al.

(10) Patent No.: US 7,629,168 B2
(45) Date of Patent: Dec. 8, 2009

(54) INSULIN EXPRESSING HUMAN PANCREATIC ISLET CELL LINE CAPABLE OF REVERSIBLY PROLIFERATING AND USE THEREOF

(75) Inventors: Noriaki Tanaka, 3235-1, Rokujoinnaka, Kamogata-cho, Asaguchi-gun, Okayama 719-0252 (JP); Naoya Kobayashi, 2033-15, Miyoshi, Okayama-shi, Okayama 703-8261 (JP); Michiki Narushima, Okayama (JP); Yoshihito Tanaka, Okayama (JP)

(73) Assignees: Noriaki Tanaka, Okayama (JP); Naoya Kobayashi, Okayama (JP); Kuraray Medical Inc., Okayama (JP)

( * ) Notice: Subject to any disclaimer, the term of this patent is extended or adjusted under 35 U.S.C. 154(b) by 346 days.

(21) Appl. No.: 10/578,260

(22) PCT Filed: Nov. 10, 2003

(86) PCT No.: PCT/JP03/14243

§ 371 (c)(1),
(2), (4) Date: May 4, 2006

(87) PCT Pub. No.: WO2005/045026

PCT Pub. Date: May 19, 2005

(65) Prior Publication Data

US 2007/0086988 A1    Apr. 19, 2007

(51) Int. Cl.
*C12P 5/06* (2006.01)
*C12P 21/06* (2006.01)
*C12P 21/04* (2006.01)
*A61K 48/00* (2006.01)

(52) U.S. Cl. .................. 435/365.1; 435/69.1; 435/70.1; 424/93.21

(58) Field of Classification Search ............... 435/365.1, 435/69.1, 70.1; 424/93.21
See application file for complete search history.

(56) References Cited

OTHER PUBLICATIONS de la Tour et al., Molecular Endocrinology, 2001, 476-483.*
Halvorsen et al., Molecular and Cellular Biology, 1999, 19: 1864-1870.*
Richards, NeuroReport, 1999, 10: i.*
Shimon, E. "Cell replacement therapy for type 1 diabetes", *Trends in Molecular Medicine*, vol. 8, No. 7, pp. 334-339 (2002).
Salmon, P., et al. "Reversible Immortalization of Human Primary Cells by Lentivector-Mediated Transfer of Specific Genes", *Molecular Therapy*, vol. 2, No. 4, pp. 404-414 (Oct. 2000).
Halvorsen, T.L., et al. "Telomerase Activity Is Sufficient To Allow Transformed Cells To Escape from Crisis", *Molecular and Cellular Biology*, vol. 19, No. 3, pp. 1864-1870, (Mar. 1999).
Zhu, J., et al. "Telomerase extends the lifespan of virus-transformed human cells without net telomere lengthening", *Proc. Natl. Acad. Sci.*, vol. 96, pp. 3723-3728, (Mar. 1999).
Westerman, K.A., et al. "Reversible immortalization of mammalian cells mediated by retroviral transfer and site-specific recombination", *Proc. Natl. Acad. Sci.*, vol. 93, pp. 8971-8976, (Aug. 1996).
O'Hare, M.J., et al. "Conditional immortalization of freshly isolated human mammary fibroblasts and endothelial cells" *Proc. Natl. Acad. Sci.*, vol. 98, No. 2, pp. 646-651, (Jan. 16, 2001).
Davies, B.R., et al. "Immortalisation of human ovarian surface epithelium with telomerase and temperature-senstitive SV40 large T antigen", Experimental Cell Research, vol. 288, pp. 390-402, (2003).
Kudo, Y., et al. "Establishment of Human Cementifying Fibroma Cell Lines by Transfectin With Temperature-sensitive Simian Virus-40 T-antigen Gene and hTERT Gene", Bone, vol. 30, No. 5, pp. 712-717, (May 2002).

\* cited by examiner

*Primary Examiner*—Ileana Popa
(74) *Attorney, Agent, or Firm*—The Nath Law Group; Susanne M. Hopkins; Charles D. Niebylski (57) ABSTRACT

A reversibly immortalized human pancreatic islet cell line containing an hTERT gene and an SV40T gene each interposed between a pair of LoxP sequences, characterized in that it is capable of producing insulin and enhancing expression of insulin after excising the hTERT gene and the SV40T gene, in particular, NAKT-13 (deposited with International Patent Organism Depository, National Institute of Advanced Industrial Science and Technology, address: AIST Tsukuba Central 6, 1-1, Higashi 1-Chome, Tsukuba-shi, Ibaraki-ken, 305-8566 Japan, deposited date: Sep. 4, 2003, accession number: FERM BP-08461) or a passage cell line thereof; a human pancreatic islet cell obtained by excising the hTERT gene and the SV40T gene from the reversibly immortalized human pancreatic islet cell line or passage cell line thereof; and use of these cells. By using the reversibly immortalized human pancreatic islet cell line of the invention insulin-producing cells can be easily and surely obtained in a number enough to meet the demand.

5 Claims, 6 Drawing Sheets
(2 of 6 Drawing Sheet(s) Filed in Color)

INSULIN EXPRESSING HUMAN PANCREATIC ISLET CELL LINE CAPABLE OF REVERSIBLY PROLIFERATING AND USE THEREOF

TECHNICAL FIELD

The present invention relates to an insulin expressing pancreatic islet cell line capable of proliferating reversibly. In particular, the present invention relates to a method for producing a therapeutic agent for diabetes and insulin.

BACKGROUND ART

Based on the cause of decline in insulin activity, diabetes is generally classified into type I diabetes (juvenile-onset diabetes) and type II diabetes.

Type I diabetes is caused by autoimmune abnormalities in which pancreatic β cells secreting insulin are specifically destroyed (see Atkinson M A, Maclaren N K., N. Engl. J. Med. 331:1428-1436, 1994). To completely treat type I diabetes, transplantation which is one of the treatments for regenerating/replacing pancreatic β cells is considered. Such transplantations include pancreas transplantation and pancreatic islet transplantation. The purposes of these two kinds of transplantation are to enable the extremely exact regulation of blood glucose, thereby preventing hypoglycemia and long-term complication from being caused. It is not the sole purpose to release patients from daily bother in insulin treatment and improve the quality of life (QOL). As a means of achieving the goal to completely treat insulin-dependent diabetes, transplantation therapy has much greater potential than insulin treatment does. However, the pancreas transplantation has problems that the operative attack is serious, and that the complications caused by concomitantly transplanted exocrine glands may be severe. In contrast thereto, the purpose of pancreatic islet transplantation is to isolate and transplant pancreatic islet β cells by excising the exocrine glands which are the cause of complications associated with transplantation operation. Presently, the pancreatic islet transplantation is a promising method for the treatment of diabetes whereby the condition of a patient is brought back to precritical condition of diabetes by the most physiological procedure. In the case of type II diabetes wherein the secretion of insulin is partially maintained, insulin shortage is also caused by hyperglycemia-induced toxicity or β cell exhaustion when the stage of disease progresses. However, pancreatic islet transplantation has not been applied for type II diabetes on the basis of the reality that pancreatic islet for transplantation is in short supply. In the future, if a great number of pancreatic islets for transplantation can be supplied, there is a great possibility that pancreatic islet transplantation is indicated for insulin-dependent diabetes with insulin resistance.

In 2000, seven cases of clinical pancreatic islet transplantation were reported from University of Alberta in Edmonton, Canada (see Shapiro A M, Lakey J R, Ryan E A, et al., N. Engl. J. Med. 343:.230-238, 2000). The report described that by a novel method for using immunosuppressant called "Edmonton Protocol" later, all the cases with type I diabetes who underwent pancreatic islet transplantation became free from administration of insulin. At the present time, pancreatic islet transplantation is the closest to an ideal treatment method for patients who suffer from insulin-dependent diabetes.

Pancreatic islet is an endocrine gland tissue and its volume is at most 2% of the whole pancreas volume. Pancreatic islet is an aggregate of endocrine cells and comprises α cells, β cells, PP cells and δ cells and the like. Insulin which is the only endogenous hormone having the effect of decreasing blood sugar, is secreted by the β cells in pancreatic islet. The β cells account for 80 to 85% of the whole cells constructing pancreatic islet. The β cells not only secret insulin but also are capable of detecting sugars in blood. The aim of pancreatic islet transplantation is to replace and regenerate a system of decreasing blood sugar which once has declined, by isolating pancreatic islet from pancreas and transplanting it to a patient who suffers from insulin-dependent diabetes.

However, in the case of pancreatic islet transplantation at the present time, there are problems of safety caused by using immunosuppressant and further serious problem, shortage of pancreatic islets for transplantation. Even though the current pancreatic islet isolating technique were improve, the number of pancreas taken from neomorts for pancreas transplantation/isolation of pancreatic islet would be much smaller than the number of patients in need thereof. Therefore, there is no prospect of overcoming the shortage problem of pancreatic islets for transplantation.

Accordingly, manufacturing cells having functions comparable to those of pancreatic islet or pancreatic islet β cells provides large contribution to society and great impact on medical economy. Besides, in stem cell research progressing with great speed in these years and attracting public attention, possibility of differentiation induction toward a pancreatic endocrine cell is indicated (see Lumelsky N, Blondel O, Laeng P, et al., Science 292: 1389-1394, 2001; Assady S, Maor G, Amit M, et al., Diabetes 50: 1691-1697, 2001), which triggers further facilitation of an interest for producing an artificial pancreatic islet β cell.

As a source of cells replacing human mature pancreatic islet β cells, human ES cells and tissue stem cells, for example, are being intensively studied at the present time. Although it was reported that insulin expression was observed by differentiation inducing in some cells (murine ES cell and hepatic stem cell), it is still unclear which gene should be transferred at which stage for secreting insulin effectively. In addition, the use of such stem cell essentially involves the difficulty in control which arises from the fact that the stem cell has pluripotency and active proliferation potency. It is considered that plenty of time is necessary to put the cells to practical use hereafter.

Study using porcine tissue/cell progresses, whereas these problems of zoonotic infection, tissue compatibility and ethics have surfaced. In particular, potential risk connected with virus has become a serious problem. For example, there is a disease-producing risk that a porcine virus contained in a porcine organ or cells infects recipient (especially, it is impossible to eliminate a porcine endogenous retrovirus (PERV), because PERV is integrated in a chromosome), and there is a novel viral infection-spreading risk that the infection spreads to its family and medical staff, and further to society.

At the present time, therefore, establishment of a tractable insulin secreting human pancreatic islet cell line which is a source of cells replacing human mature pancreatic islet β cells is desired. Until now, many researchers have made aggressive efforts to immortalize a human pancreatic islet cell, but any human pancreatic islet cell line producing insulin has not been reported at all. Possible explanations are as follows; 1) gene transfer is difficult because insulin producing β cells exist in the inside of pancreatic islet, 2) cell-life extension is taken place but the complete immortalization of cells cannot be achieved because a tumor gene originated from a virus (such as a simian virus 40 tumor antigen) is used to establish an immortalized cell line. In fact, the frequency that human cells proliferate without limitation beyond proliferation decay is low (see Shay J W, Wright W E, Exp. Cell Res. 184: 109-118, 1989; Ray F A, Kraemer P M, Carcinogenesis 14: 1511-1516, 1993). Furthermore, it is reported that a probability of natural immortalization in a cell using SV40T in vitro is about $3.3 \times 10^{-7}$; it is said that the cell further needs natural expression of autogenic telomerase activity (see, Bondar A G, Science 279: 349-352, 1998; Zhu J, et al., Proc. Natl. Acad. Sci. USA 96: 3723-3728, 1999; Halvorsen T L, et al., Mol. Cell. Biol. 19: 1864-1870, 1999).

An object of the present invention is to solve the problems in the prior art, and to provide a human pancreatic islet cell line capable of producing insulin and enabling easy obtainment of the number of cells which meets the demand.

DISCLOSURE OF INVENTION

As a result of an intensive study to solve the above problems, we have found the followings and completed the present invention. It has been found that by transferring a recombinant retroviral vector SSR#197 (see Watanabe T, et al., Transplantation 15; 75 (11): 1873-1880, 2003) expressing a human telomerase reverse transcriptase (hereinafter referred to as "hTERT gene") and a recombinant retroviral vector SSR#69 (Westerman K A, Leboulch P., Proc. Natl. Acad. Sci. USA 93: 8971-8976, 1996) expressing a simian virus 40 tumor antigen gene (hereinafter referred to as "SV40T gene") into an isolated healthy human pancreatic islet cell, an immortalized cell line characterized in that it is capable of reversibly proliferating, producing insulin and enhancing expression of insulin after excision of the hTERT gene and the SV40T gene, can be established.

That is to say, the present invention relates to an reversibly immortalized human pancreatic islet cell line or a passage cell line thereof, containing an hTERT gene and an SV40T gene each interposed between a pair of LoxP sequences, the cell line being capable of producing insulin and enhancing expression of insulin after excision of the hTERT gene and the SV40T gene.

The reversibly immortalized human pancreatic islet cell line is preferably NAKT-13 (deposited with International Patent Organism Depository, National Institute of Advanced Industrial Science and Technology, address: AIST Tsukuba Central 6, 1-1, Higashi 1-Chome, Tsukuba-shi, Ibaraki-ken, 305-8566 Japan, deposited date: Sep. 4, 2003, accession number: FERM BP-08461).

The present invention also relates to a human pancreatic islet cell obtained by excising the hTERT gene and the SV40T gene from the reversibly immortalized human pancreatic islet cell line or the passage cell line thereof.

Furthermore, the present invention relates to a therapeutic agent for diabetes, comprising a human pancreatic islet cell obtained by excising the hTERT gene and the SV40T gene from the reversibly immortalized human pancreatic islet cell line or the passage cell line thereof.

The present invention also relates to a method for producing insulin, comprising utilizing the reversibly immortalized human pancreatic islet cell line or the passage cell line thereof, or the human pancreatic islet cell obtained by excising the hTERT gene and the SV40T gene from the reversibly immortalized human pancreatic islet cell line or passage cell line thereof.

BRIEF DESCRIPTION OF DRAWINGS

The application file contains at least one drawing executed in color. Copies of this patent application with color drawings (s) will be provided by the Office upon request and payment of the necessary fee.

BEST MODE FOR CARRYING OUT THE INVENTION

In the present invention, the terms "reversibly immortalized" or "capable of reversibly proliferating" means that a cell is brought into a condition capable of proliferating immortally by transducing an immortalizing gene into the cell; after proliferation of the cells up to a desired cell number, the cell division is arrested by excising the immortalizing gene so that the condition of the cell is reverted to the former condition with high safety.

Figure 1:
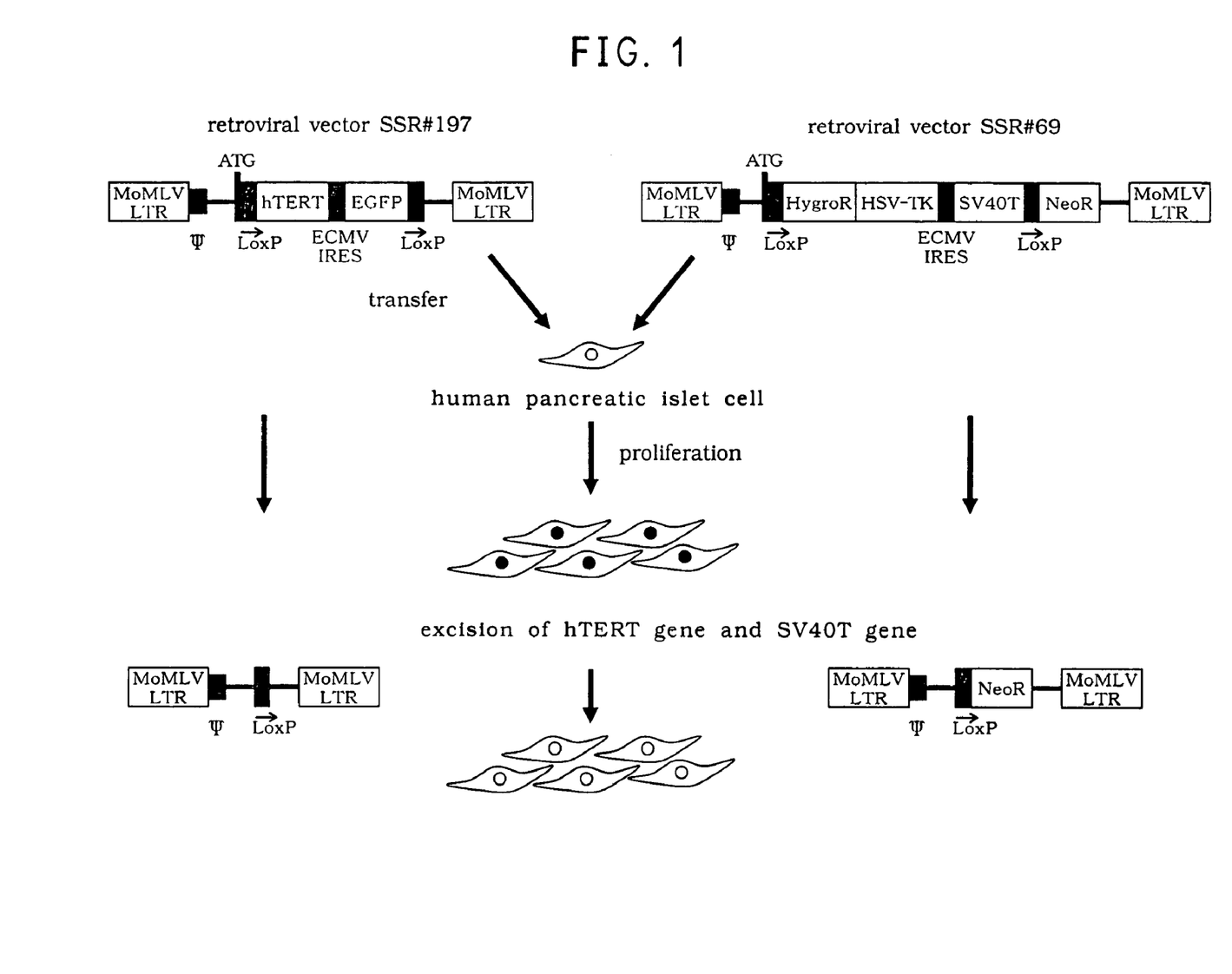
FIG. 1 is a schematic view showing a method for producing a reversibly immortalized human pancreatic islet cell line in accordance with the present invention and a method for producing a human pancreatic islet cell obtained by excising the hTERT gene and the SV40T gene from the reversibly immortalized human pancreatic islet cell line in accordance with the present invention. Herein, ATG indicates starting codon, ψ packaging signal, LoxP LoxP sequence, hTERT hTERT gene, EGFP enhanced green fluorescent protein gene, MoMLV LTR Moloney murine leukemia virus long terminal repeat, ECMV IRES encephalomyocarditis virus internal ribosome entry site, HygroR hygromycin-resistant gene, HSV-TK herpes simplex virus-thymidine kinase, SV40T SV40T gene, NeoR neomycin-resistant gene, respectively.
Figure 2:
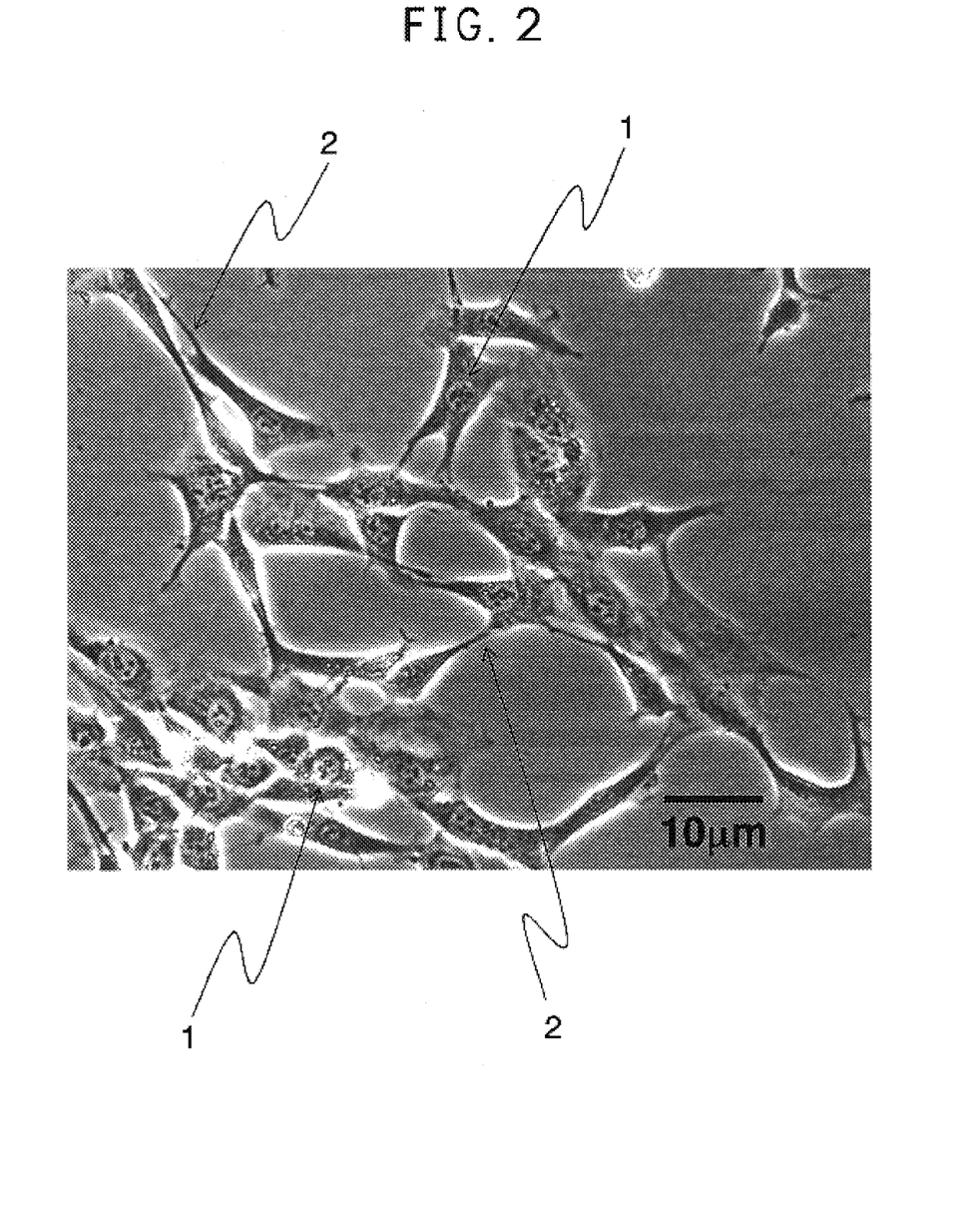
FIG. 2 is a phase-contrast microscope image of the NAKT-13 cell (deposited with International Patent Organism Depository, National Institute of Advanced Industrial Science and Technology, address: AIST Tsukuba Central 6, 1-1, Higashi 1-Chome, Tsukuba-shi, Ibaraki-ken, 305-8566 Japan, deposited date: Sep. 4, 2003, accession number: FERM BP-08461). Portion 1 denotes a nucleus and Portion 2 denotes a neuroendocrine cell-like apophysis.

The reversibly immortalized human pancreatic islet cell lines of the present invention is a human pancreatic islet cell line containing an hTERT gene and an SV40T gene each interposed between a pair of LoxP sequences. For more detail, the cells are obtained by transferring a retroviral vector SSR#197 containing the hTERT gene interposed between a pair of LoxP sequences and a retroviral vector SSR#69 containing the SV40T gene interposed between a pair of LoxP sequences into an isolated healthy human pancreatic islet cells, the cells are capable of producing insulin and enhancing expression of insulin after excision of the hTERT gene and the SV40T gene. Among them, the NAKT-13 cell line (deposited with International Patent Organism Depository, National Institute of Advanced Industrial Science and Technology, address: AIST Tsukuba Central 6, 1-1, Higashi 1-Chome, Tsukuba-shi, Ibaraki-ken, 305-8566 Japan, deposited date: Sep. 4, 2003, accession number: FERM BP-08461) is preferable. The reversibly immortalized pancreatic islet cell of the present invention has characteristics of a neuroendocrine cell, such as being of a small size and extending an apophysis (Portion 2) as shown in FIG. 2 (the NAKT-13 cell (deposited with International Patent Organism Depository, National Institute of Advanced Industrial Science and Technology, address: AIST Tsukuba Central 6, 1-1, Higashi 1-Chome, Tsukuba-shi, Ibaraki-ken, 305-8566 Japan, deposited date: Sep. 4, 2003, accession number: FERM BP-08461)).

The isolated healthy human pancreatic islet cell employed in the present invention can be isolated from a human pancreas by a conventional method (see Staudacher C, Ricordi C, Stella M, Socci C, Cammelli L, Ferrari G, Dicarlo V, Minerva Chir. 31: 1665-1668, 1985 or Ricordi C, Finke E H, Lacy P E., Diabetes 35: 649-653, 1986).

The term "enhancing expression of insulin" means that the expression of insulin in a cell increases by excising the immortalizing gene, compared with the cell before excision. For example, 2 to 100 fold increase is preferable.

The expression of insulin can be evaluated by conventional methods, for example, an insulin immunostaining procedure utilizing an insulin antibody. The amount of expression can be compared by measuring a fluorescence intensity of an insulin-stained sample. To compare this fluorescence intensity, an image processing analyzing software NIH image (vol. 62) (available from NIH (National Institute of Health) in USA, without charge) and the like, can be used.

A retroviral vector SSR#197 encodes an enhanced green fluorescent protein (GFP) gene in addition to the hTERT gene, a retroviral vector SSR#69 encodes a fusion gene comprising a hygromycin-resistant gene (HygroR) and a herpes simplex virus-thymidine kinase gene (HSV-TK); and a neomycin-resistant gene (NeoR) in addition to the SV40T gene. Each of these vectors can be manufactured in accordance with conventional methods, for example, those described in the above-mentioned Watanabe T, et al., Transplantation 15; 75(11): 1873-1880, 2003 and Westerman K A, Leboulch P., Proc. Natl. Acad. Sci. USA 93: 8971-8976, 1996.

The above-mentioned LoxP sequence is a known site-specific recombination sequence recognized by a Cre recombinase. Between the sequences, performed is homologous recombination comprising the steps of excising, exchanging and coupling of DNA-strands. When a pair of LoxP sequences is present in the same direction in a same DNA molecule, the DNA sequence interposed by the sequences is excised to become a circular molecule (excision reaction).

The above-mentioned hTERT gene is originated from a TERT gene in a normal cell. The hTERT gene is a gene whose expression is naturally enhanced in a stem cell and a progenitor cell in organs regenerating repeatedly over lifetime such as blood, skin, intestinal mucosa, endometrium and the like, and in a lymphocyte proliferating clonally when ever exposed to a specific antigen.

The above-mentioned SV40T gene is a tumor antigen (T antigen) gene of a known DNA-type tumor virus.

Transferring a retroviral vector SSR#197 and a retroviral vector SSR#69 are carried out by a method of inoculating these retroviral vectors directly on culture cells.

As the procedure for transferring the retroviral vector into the culture cells by inoculating the retroviral vector directly upon culture cells, any procedure can be used as long as the procedure achieves the object of the present invention. For example, the transferring of the retroviral vector can be performed by culturing cells producing the retroviral vector, and then inoculating the resulting cultural supernatant upon pancreatic islet cells cultured separately. Various conditions such as culture condition and inoculating density for respective cells can be determined according to the method well known in the art.

In addition, it is preferable that the inoculation of the vector upon the culture cell is conducted only once, taking into consideration effects on the cell, for example, stability of the chromosome. However, taking into consideration the vector-transfer efficiency, it is preferable that the number of time of the inoculation upon the cell is larger. Based on these facts, it is the most preferable in the present invention to perform four-hour-infection twice a day, for 3 days in total.

Cre recombinase herein is a known recombinase which specifically recognizes LoxP sequence. Cre recombinase should not be limited as long as it excises the nucleotide sequence interposed by the LoxP sequences. According to the present invention, Cre recombinase is used to excise the hTERT gene and the SV40T gene interposed by the LoxP sequences located in the chromosome in the reversibly immortalized human pancreatic islet cell line. The cells obtained by excising the hTERT gene and the SV40T gene interposed by the LoxP sequences from the chromosome in reversibly immortalized pancreatic islet cells are safe without risks of malignant transformation and are suitable for cell transplantation.

Examples of the methods for excising the hTERT gene and the SV40T gene from the reversibly immortalized human pancreatic islet cell line, which was cultured on a large scale in vitro, by using the Cre recombinase, include (1) a method wherein the Cre recombinase is transduced by an adenoviral vector having high gene-transfer efficiency, (2) a method wherein the Cre recombinase DNA is added to the cell culture medium by calcium phosphate transfection, (3) a method wherein a fusion protein comprising a TAT protein originated from a human immunodeficiency virus (HIV) and the Cre recombinase is added to the culture supernatant, (4) a method wherein a cationized Cre recombinase is added to the cell culture medium, and (5) a method wherein a system capable of excising the gene by addition of a drug is added by transferring a drug-induced Cre recombinase expression vector. The methods using no adenoviral vector are more preferable, because further superinfection by a viral vector is not required.

Figure 5:
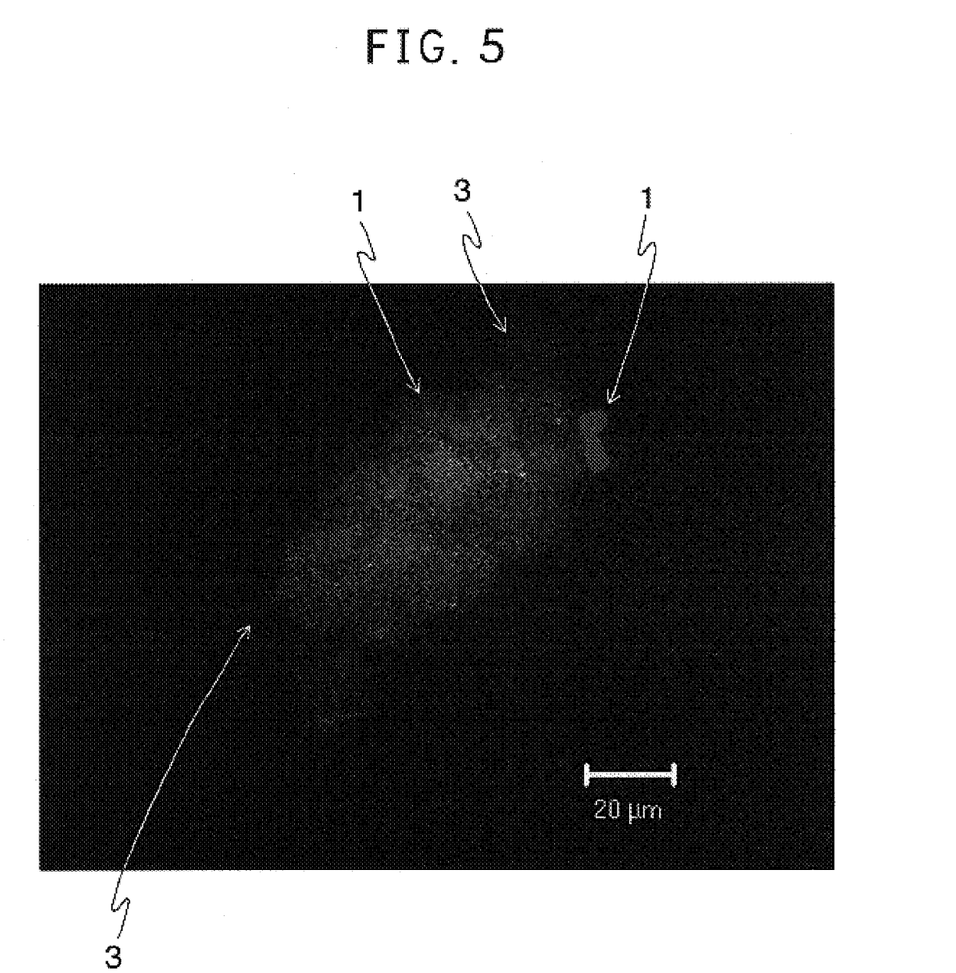
FIG. 5 is a photograph of an AxCANCre treated NAKT-13, stained by the insulin immunostaining method. All of Portions 1 visible in red regardless of thickness denote nuclei and all of Portions 3 visible in green regardless of thickness denote insulin.

A human pancreatic islet cell (hereinafter referred to as "reverted human pancreatic islet cell") obtained by excising the hTERT gene and the SV40T gene from the reversibly immortalized human pancreatic islet cell line in accordance with the present invention, is enhanced in expression of insulin, for example, as shown in FIG. 5 (the reverted NAKT-13 cells), and naturally aggregates each other to possess a morphological feature similar to normal pancreatic islet structure.

The therapeutic agent for diabetes of the present invention can be used as a cell preparation comprising the reverted human pancreatic islet cell. The therapeutic agent for diabets of the present invention may contain an ingredient used for treating diabetes as another active ingredient in addition to the reverted human pancreatic islet cell. For the active ingredient, troglitazone or the like can be used. In order to facilitate the secretion of insulin, it is preferable to add nicotinamide. The cell preparation herein means to include a suspension obtained by suspending the human pancreatic islet cell into a culture medium, an isotonic solution or a buffer, and a clump of cells such as a concentrated pellet or the like by centrifugation or the like. The culture medium, the isotonic solution or the buffer is selected properly to adapt to the human pancreatic islet cell. Furthermore, the cell preparation can be cryopreserved by addition of a protecting agent such as DMSO. In view of inoculating the cell preparation into a human body, the deletion of the ability of cell proliferation makes the cell preparation safer. In order to use the cells as a cell preparation more safely, it is possible to treat the cells by heat treatment, radiation treatment, mitomycin C treatment or the like, under the conditions which the function as a cell preparation is kept and a pathogenic cell protein is degenerated.

In case that the reverted human pancreatic islet cell is transplanted, it is preferable that the cell is transplanted into liver through portal vein. Examples of the transplantation method include a method wherein a small incision is made in the right hypogastrium, a mesenteric thin blood vessel is exteriorized and a catheter is inserted into the blood vessel to transplant the cells under direct vision, and a method wherein the portal vein of liver is located by means of ultrasound echo and a catheter is punctured thereinto to transplant the cells. Among these methods, the cell transplantation methods using ultrasound echo is preferable because of less invasion.

The amount of the therapeutic agent administered (transplanted) is, for example, preferably $1\times10^8$ to $1\times10^{10}$ cells/indivisual, more preferably $1\times10^9$ to $1\times10^{10}$ cells/indivisual, and most preferably $1\times10^9$ to $2\times10^9$ cells/indivisual.

The reversibly immortalized human pancreatic islet cell line and the reverted human pancreatic islet cell of the present invention can be used, for example, as a diabetes-targeted medical transplantation or as a source of a bioartificial pancreas. Examples of the medical transplantation or the bioartificial pancreas include hybrid artificial pancreases obtained by combining isolated/cultured cells with a module (device) wherein the insulin-secreting cells are sealed in a device made of a polymer material such as diffusion-chamber type, microcapsule type or hollow-fiber type. The bioartificial pancreas includes three embodiments: one which is attached to the outside of the body with connecting to blood vessel; one which is indwelled within the body with connecting to blood vessel; and one which is indwelled within the abdominal cavity without connecting to blood vessel. The reversibly immortalized human pancreatic islet cell and the reverted human pancreatic islet cell of the present invention can be used for any embodiment of the bioartificial pancreases.

Furthermore, both of the reversibly immortalized pancreatic islet cell and the reverted human pancreatic islet cell of the present invention can be used for producing insulin. Since the reverted human pancreatic islet cell is enhanced in the expression of insulin, it is preferable to produce insulin effectively by culturing the reversibly immortalized pancreatic islet cells in large quantities and obtaining the reverted cells by excising the hTERT gene and the SV40T gene.

The production of insulin can be performed by removing the cells from the cell culture and purifying the culture fluid by a method usually used for protein purification such as affinity column chromatography.

The present invention will be explained specifically by means of the following Examples. However, it is to be understood that the invention is not limited to only these Examples.

EXAMPLE 1

Establishment of the Reversibly Immortalized Human Pancreatic Islet Cell Line NAKT-13 (Deposited with International Patent Organism Depository, National Institute of Advanced Industrial Science and Technology, Address: AIST Tsukuba Central 6, 1-1, Higashi 1-Chome, Tsukuba-Shi, Ibaraki-Ken, 305-8566 Japan, Deposited Date: Sep. 4, 2003, Accession Number: FERM BP-08461)

Spherical cells (10 cells) with good-looking conformation were selected from isolated healthy human pancreatic islet cells provided from Alberta University, Canada (available to everyone from Dr. Jonathan R T. Lakey, Human Pancreatic Islet Transplantation Program, Alberta University, Canada) by hand pickup method under stereomicroscope (STEMI, made by Carl Zeiss, Germany), and inoculated in a T25-culture flask. As a basal culture medium, a medium composed of William's MEDIUM E (available from SIGMA, Saint Louis, USA) supplemented with 10% of fetal calf serum (FCS, available from SIGMA), $10^{-7}$ mol/l of insulin (available from SIGMA), $10^{-6}$ mol/l of dexamethasone (available from SIGMA), 25 µg/ml of epithelial growth factor (EGF, available from SIGMA), 10 mM of nicotinamide (available from SIGMA) and antibiotics penicillin G/streptomycin (available from SIGMA) was used. Until the 3rd day from the inoculating, 4 ml of the basal culture medium was used and the medium was not exchanged. On or after 4th day from the inoculating, when the medium was exchanged, 2 ml of the basal culture medium, 1 ml of a solution obtained by filtering a cultural supernatant of a retroviral vector SSR#69 producing cell with a 0.45 µm filter and 1 ml of a solution obtained by filtering a cultural supernatant of a retroviral vector SSR#197 producing cell with a 0.45 µm filter, 4 ml in total, were added and incubated for four hours. This gene transfer was conducted twice a day. This manipulation was repeated on 4th day, 6th day and 8th day (6 times in total) in the same manner.

Furthermore, the cultural supernatants of the retroviral vector SSR#197 producing cell and the retroviral vector SSR#69 producing cell were prepared as follows.

Crip cells producing the retroviral vector SSR#197 (SSR#197) (Watanabe T, et al., Transplantation 15; 75 (11): 1873-1880, 2003) (titer was $4\times10^6$ cfu/ml) and Crip cells producing the retrovial vector SSR#69 (SSR#69) (Westerman K A, Leboulch P., Proc. Natl. Acad. Sci. USA 93: 8971-8976, 1996) (titer was $4\times10^6$ cfu/ml), both provided from Dr. Philippe Leboulch (Harvard-Massachusetts Institute of Technology, Cambridge Mass., USA) were used. Each of the Crip cells were inoculated in a culture T75-flask at $1\times10^5$ cells/cm$^2$ and cultured in 10 ml of a medium composed of DMEM+10% of NCS (newbone calf serum). When the cell density was up to about 90%, the medium was exchanged by 10 ml of a fresh medium composed of DMEM+10% of NCS. The incubation was conducted for 24 hours after exchange of the medium to give the cultural supernatant containing the retroviral vector SSR#197 or the retroviral vector SSR#69.

On or after 10th day from the inoculating of the human pancreatic islet cell (2nd day from the last infection), the basal culture medium was changed to a medium composed of DMEM low glucose (available from Gibco, Auckland, N.J.) supplemented with 10% of FCS, 10 mM of nicotinamide, 320 µl/l of hygromycin and penicillin G/streptomycin, and then the cells were screened with 100 µg/ml of hygromycin (available from SIGMA). When a hygromycin-resistant cell line appeared, the cell was cloned by using cloning ring. When each cloned cell was proliferated, GFP-positive cells were collected by using a flow cytometer MoFlo (made by Dako-Cytomation Co. LTD., Kyoto, Japan), thereby establishing the reversibly immortalized human pancreatic islet cell line NAKT-13 (deposited with International Patent Organism Depository, National Institute of Advanced Industrial Science and Technology, address: AIST Tsukuba Central 6, 1-1, Higashi 1-Chome, Tsukuba-shi, Ibaraki-ken, 305-8566 Japan, deposited date: Sep. 4, 2003, accession number: FERM BP-08461). NAKT-13 was deposited to International Patent Organism Depository, National Institute of Advanced Industrial Science and Technology (address: AIST Tsukuba Central 6, 1-1, Higashi 1-Chome, Tsukuba-shi, Ibaraki-ken, 305-8566 Japan, deposited date: Sep. 4, 2003, accession number: FERM BP-08461). The obtained cell line NAKT-13 (deposited with International Patent Organism Depository, National Institute of Advanced Industrial Science and Technology, address: AIST Tsukuba Central 6, 1-1, Higashi 1-Chome, Tsukuba-shi, Ibaraki-ken, 305-8566 Japan, deposited date: Sep. 4, 2003, accession number: FERM BP-08461) has characteristics of a neuroendocrine cell being of a small size and extending an apophysis (portion 2) as shown in FIG. 2.

EXAMPLE 2

Excision of SV40T Gene and hTERT Gene from Reversibly Immortalized Human Pancreatic Islet Cell Line The reversibly immortalized human pancreatic islet cell line obtained in Example 1 was cultured at $10^5$ cells/ml in a medium composed of DMEM low glucose (available from Gibco, Auckland, N.J.) supplemented with 10% of FCS, 10 mM of nicotinamide and penicillin G/streptomycin. Twenty-four hours after incubation start-up, an adenoviral expression vector AxCANCre encoding a Cre recombinase was added to the medium at 1 MOI (multiplicity of infection), followed by persistent infection for forty hours. The cells obtained were washed twice with PBS and then the medium was exchanged. As shown in FIG. 5, the reverted NAKT-13 cells are characterized in that they naturally aggregate each other and have morphological feature similar to a normal pancreatic islet structure.

EXAMPLE 3

Expression of Insulin and Morphological Feature

The cells obtained in Example 1 or 2 ($10^5$ cells, respectively) were inoculated on a cover slide put on a 6-well plate and cultured up to 60% of cell density for twenty-four hours in a medium composed of DMEM low glucose (available from Gibco, Auckland, N.J.) supplemented with 10% of FCS, 10 mM of nicotinamide and penicillin G/streptomycin. The medium was then changed to a medium composed of DMEM high glucose (available from Gibco, Auckland, N.J.) supplemented with 10% of FCS, 10 mM of nicotinamide and penicillin G/streptomycin and the cells were cultured for six hours.

Figure 3:
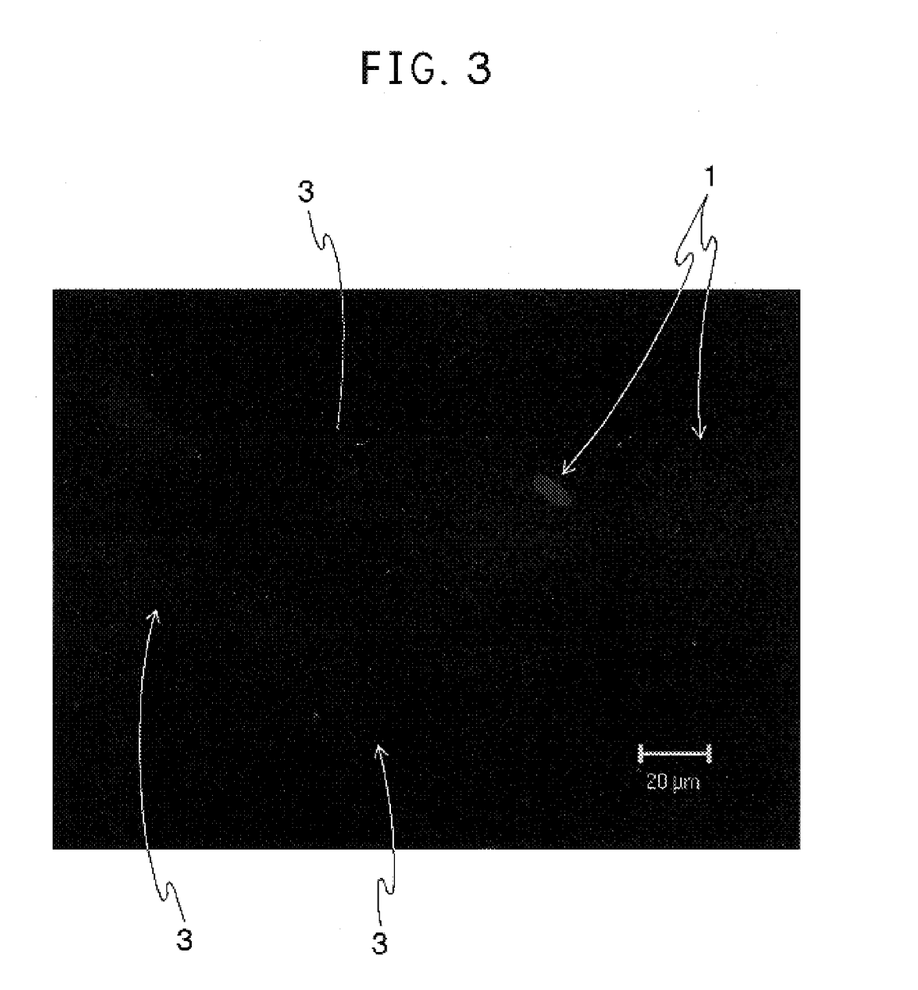
FIG. 3 is a photograph of the NAKT-13 cell (deposited with International Patent Organism Depository, National Institute of Advanced Industrial Science and Technology, address: AIST Tsukuba Central 6, 1-1, Higashi 1-Chome, Tsukuba-shi, Ibaraki-ken, 305-8566 Japan, deposited date: Sep. 4, 2003, accession number: FERM BP-08461) stained by an insulin immunostaining procedure. All of Portions 1 visible in red regardless of thickness denote nuclei and all of Portions 3 visible in green regardless of thickness denote insulin.
Figure 4:
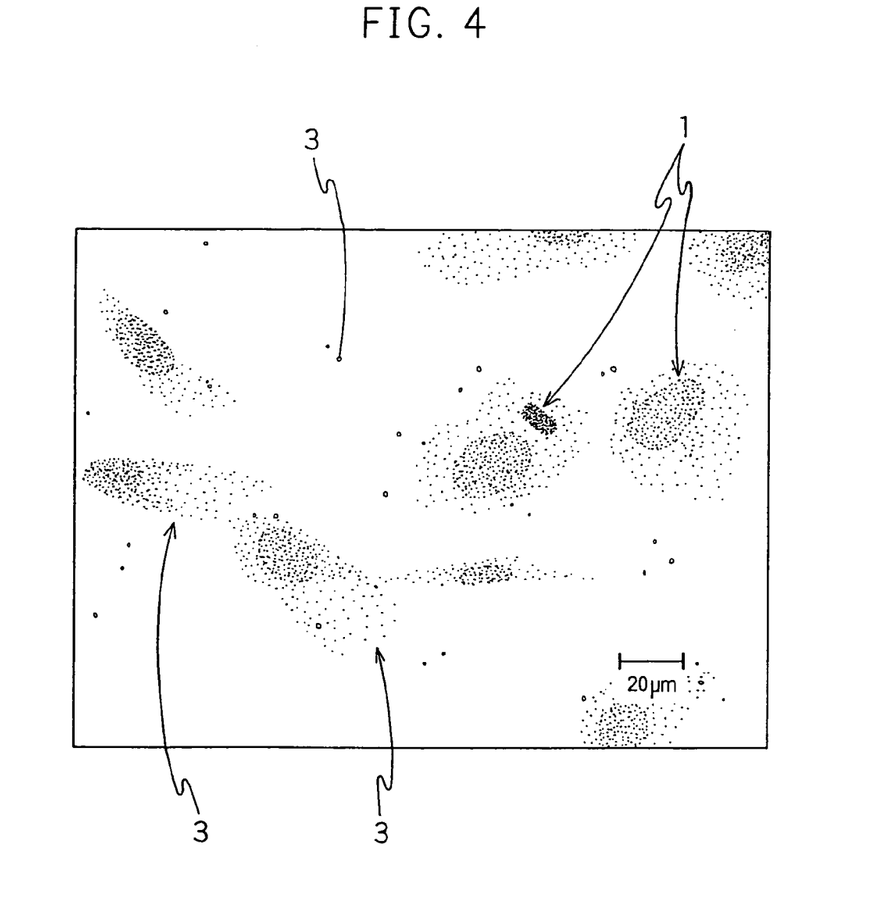
FIG. 4 is a sketch of FIG. 3 in order to show the cell nuclei and the insulin more apparently. Numeral 1 corresponds to 1 in FIG. 3, which denotes the nucleus. Numeral 3 corresponds to 3 in FIG. 3, which denotes insulin.
Figure 6:
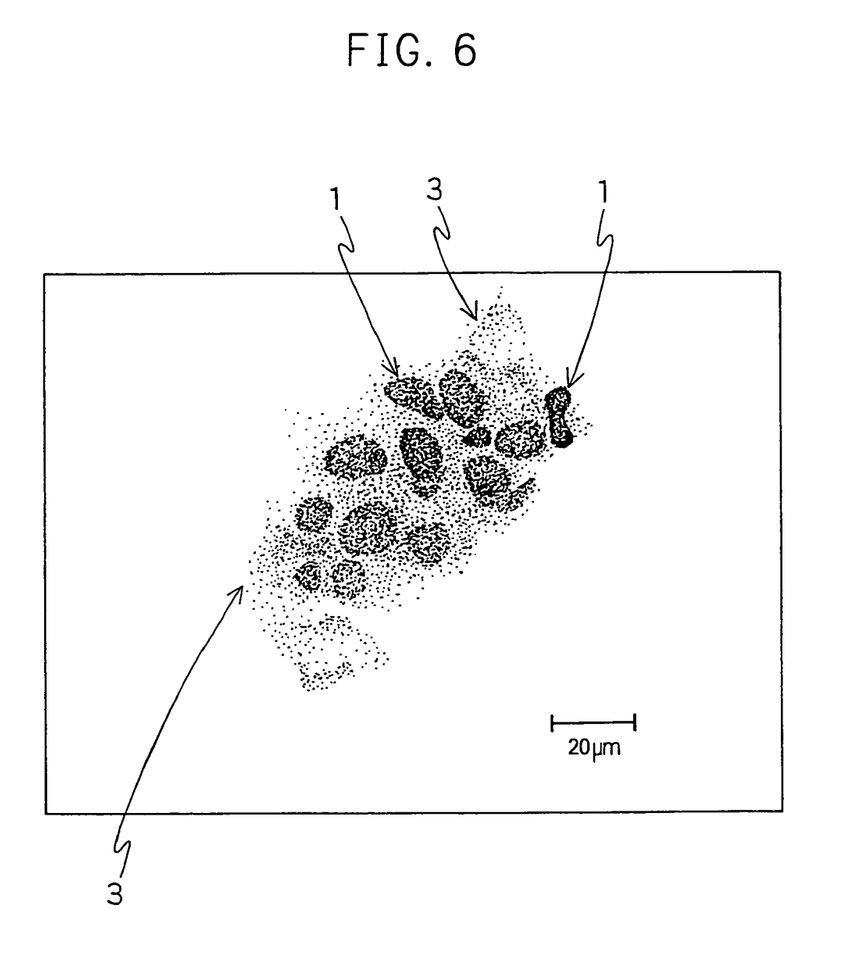
FIG. 6 is a sketch of FIG. 5 in order to show the cell nuclei and the insulin more apparently. Numeral 1 corresponds to 1 in FIG. 5, which denotes the nucleus. Numeral 3 corresponds to 3 in FIG. 5, which denotes insulin.

After the culture was completed, the expression of insulin in the cells was examined by an immunostaining method using a rabbit anti-human insulin antibody (available from DakoCytomation, Co., LTD., Kyoto, Japan). The staining results are shown in FIGS. 3 and 5. FIGS. 4 and 6 are sketches of FIGS. 3 and 5, respectively. FIGS. 3 and 5 show the NAKT-13 cells (deposited with International Patent Organism Depository, National Institute of Advanced Industrial Science and Technology, address: AIST Tsukuba Central 6, 1-1, Higashi 1-Chome, Tsukuba-shi, Ibaraki-ken, 305-8566 Japan, deposited date: Sep. 4, 2003, accession number: FERM BP-08461) obtained in Example 1 and the reverted NAKT-13 cells obtained in Example 2, respectively. In FIGS. 3 and 5, all of Portions 1 visible in red regardless of thickness denote cell nuclei and all of Portions 3 visible in green regardless of thickness denote insulin.

From FIG. 3, the expression of insulin in the NAKT-13 cell (deposited with International Patent Organism Depository, National Institute of Advanced Industrial Science and Technology, address: AIST Tsukuba Central 6, 1-1, Higashi 1-Chome, Tsukuba-shi, Ibaraki-ken, 305-8566 Japan, deposited date: Sep. 4, 2003, accession number: FERM BP-08461) obtained in Example 1 was confirmed. From FIGS. 3 and 5, it was confirmed that the expression of insulin of the reverted NAKT-13 cells obtained in Example 2 increased markedly, i.e. by about 30 times that of the pre-reverted immortalized pancreatic islet cells, by comparing the fluorescence intensity using an image processing analyzing software NIH image (vol. 62) (available from NIH in USA, without charge).

INDUSTRIAL APPLICABILITY

According to a reversibly immortalized human pancreatic islet cell line of the present invention, cells having an insulin-producing activity can be easily and surely obtained in a number enough to meet the demand. Besides, a reverted human pancreatic islet cell obtained by excising the hTERT gene and the SV40T gene from the cell line, is extremely useful for treating diabetes, because the cell shows an enhanced expression of insulin and is safe.

In addition, on the basis of utilizing cells of the present invention, it is possible to produce insulin or to develop a bioartificial pancreas such as a hybrid artificial pancreas obtained by combining isolated/cultured cells with a module (device) such as diffusion-chamber type, micro-capsule type or hollow-fiber type.

The invention claimed is:

1. An NAKT-13 cell line or a passage cell line thereof wherein the passage cell line thereof retains NAKT-13 cell line characteristics, comprising: a hTERT gene and a SV40T gene each interposed between a pair of LoxP sequences, the cell line being capable of producing insulin and enhancing expression of insulin after excision of the hTERT gene and the SV40T gene.

2. A method of preparing a human pancreatic islet cell comprising:
   providing the NAKT-13 cell line or a passage cell line thereof of claim 1;
   excising the hTERT gene and the SV40T gene from the cell line ex vivo; and
   purifying the resulting cell line.

3. A method for treating diabetes, comprising:
   providing the NAKT-13 cell line or a passage cell line thereof of claim 1;
   excising the hTERT gene and the SV40T gene from the cell line ex vivo;
   administering an effective amount of the cell line after excision to a patient in need thereof.

4. A method for producing insulin, comprising:
   culturing the NAKT-13 cell line or a passage cell line thereof of claim 1 in a culture medium under conditions sufficient to express insulin; and
   purifying insulin from the culture medium to obtain insulin.

5. A method for producing insulin, comprising:
   culturing the human pancreatic islet cell prepared by the method of claim 2 in a culture medium under conditions sufficient to express insulin; and
   purifying insulin from the culture medium to obtain insulin.

* * * * *